United States Patent [19]
Leonardi

[11] Patent Number: 5,183,059
[45] Date of Patent: Feb. 2, 1993

[54] EYE SHIELD RETENTION SYSTEM

[76] Inventor: David Leonardi, 2927 S. Industrial Rd., Las Vegas, Nev. 89109

[21] Appl. No.: 821,799

[22] Filed: Jan. 16, 1992

Related U.S. Application Data

[63] Continuation-in-part of Ser. No. 467,684, Jan. 19, 1990, abandoned.

[51] Int. Cl.$^5$ ............................................... A61F 9/00
[52] U.S. Cl. .................................. 128/858; 604/308; 602/74; 2/15
[58] Field of Search ............... 128/858, 857, 793, 888; 2/15, 426, 452; 602/74; 604/308, 364

[56] References Cited

U.S. PATENT DOCUMENTS

| | | | |
|---|---|---|---|
| 591,244 | 10/1897 | Wylie . | |
| 973,158 | 10/1910 | Berthel | 602/74 |
| 1,161,321 | 11/1915 | Lush . | |
| 1,553,010 | 9/1925 | Terry et al. | 2/15 |
| 1,758,764 | 5/1930 | Roxburg | 128/163 |
| 2,024,491 | 1/1935 | Veysey | 128/163 |
| 2,389,223 | 11/1945 | Werner | 2/15 |
| 2,643,382 | 6/1953 | McLeod | 2/15 |
| 2,891,252 | 6/1959 | Lazo | 2/15 |
| 4,502,476 | 3/1985 | Welt | 602/74 |
| 4,564,960 | 1/1986 | Nishiyama | 2/452 |
| 4,677,974 | 7/1987 | Leonardi | 128/163 |
| 4,727,869 | 3/1988 | Leonardi | 128/163 |

Primary Examiner—Robert A. Hafer
Assistant Examiner—David J. Kenealy
Attorney, Agent, or Firm—John Edward Roethel

[57] ABSTRACT

An improved eye shield retention system holds a generally ovate eye cover in position across the bony orbital rim of a user's eye. The eye shield comprises a plastic shell adapted to function as an eye shield or as a backup member for an eyelid compress. The retention system has a first strap segment that attaches to the lower end of the eye shield and joins with a second strap segment behind the user's head. The second strap segment attaches to the upper end of the eye shield and is bifurcated into an upper and lower strap segment adapted to encircle a user's head either in an adjacent and parallel relationship or to be laterally separated to cause the two strap segments to oppose one another against the curvature of the user's skull. In the latter condition the strap segments prevent the eye shield retention system from slipping into a less than snug fit over the skull in which the eye cover could become dislodged. The invention further includes various modifications of this retention system such as both the first and second strap segments being bifurcated or such as the strap retention system comprising a continuous strap with one segment bifurcated and the other being a solid piece.

25 Claims, 4 Drawing Sheets

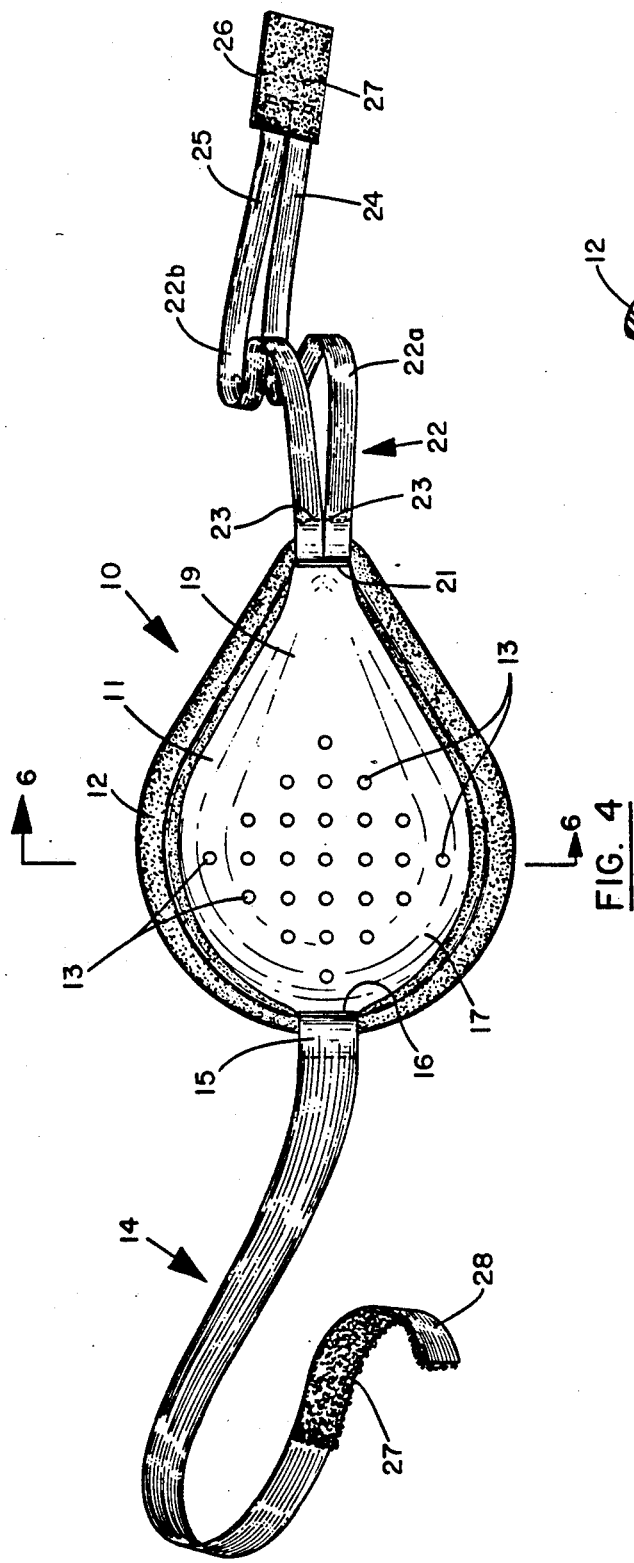
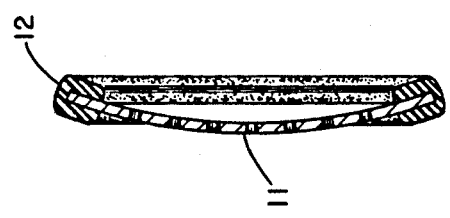
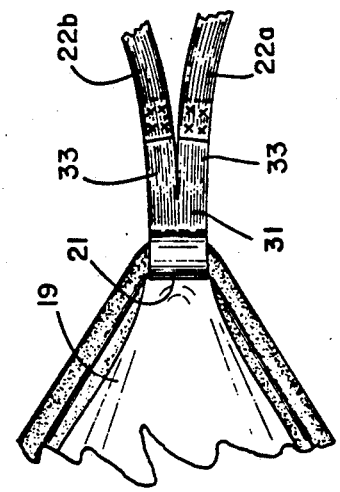
FIG. 4
FIG. 5
FIG. 6

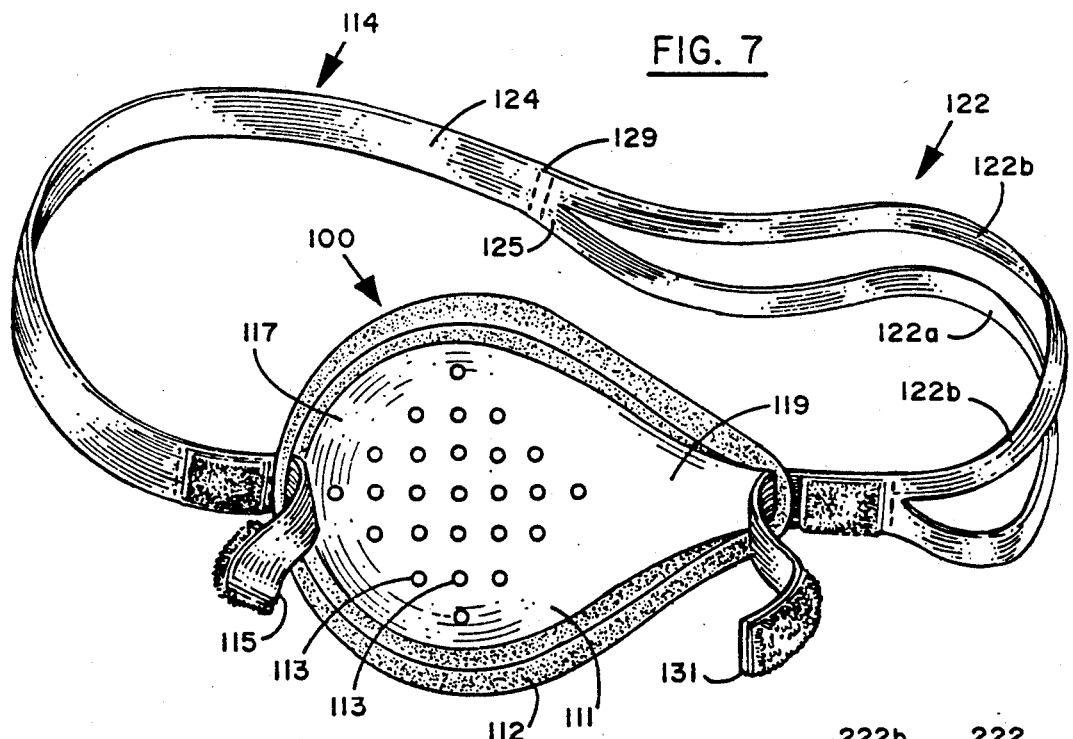
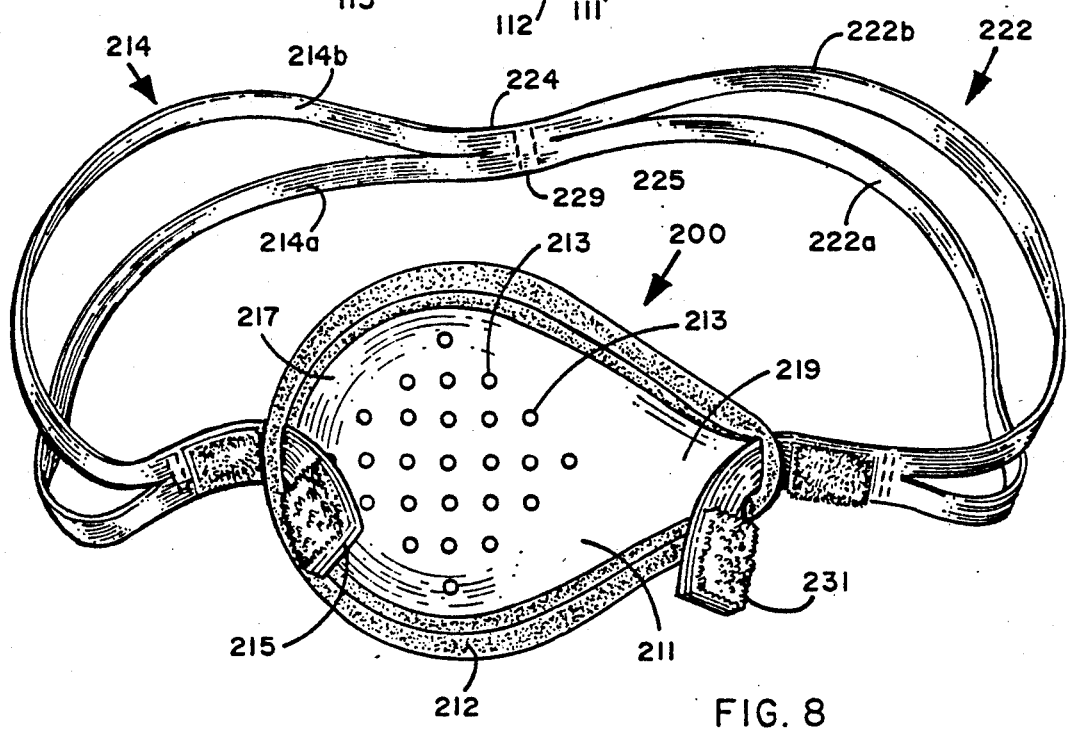

EYE SHIELD RETENTION SYSTEM

CROSS-REFERENCE TO RELATED APPLICATION

This application is a Continuation-in-Part of copending application Ser. No. 07/467,684, filed Jan. 19, 1990 now abandoned.

This invention relates to an improved eye shield retention system for holding a generally ovate eye cover such as an eye shield or eyelid splint backing member in an eye covering position across the bony orbital rim of a user's eye when the use of such an eye cover is required during treatment of an injured or diseased eye.

BACKGROUND OF THE INVENTION

Wylie, U.S. Pat. No. 591,244; Lush U.S. Pat. No. 1,161,321 and Werner U.S. Pat. No. 2,389,223 are early examples of eye shield retention systems utilizing a strap adapted to encircle the user's head to hold an eye shield in place. More recent versions of eyelid splints, as distinguished from eye shields, also utilize a strap to hold the eyelid splint backing member and thereby the eyelid splint in place on the user's head. Reference is made to Leonardi's U.S. Pat. Nos. 4,677,974 and No. 4,727,869.

The known strap retention systems have a weakness in that the straps fail to fully retain the eye shield or the eyelid splint in place on the user's head if the user makes vigorous head movements or if the user's head rubs against a pillow while sleeping.

Accordingly it is an object of the present invention to provide a eye shield retention system that will securely hold an eye shield or eyelid splint on the user's head with maximum comfort and efficacy while the user is engaged in strenuous activities or while the user is asleep.

It is a further object to provide an improved eye shield or eyelid splint retention system that can be manufactured at no significant cost penalty over the strap systems currently known.

It is a further object to provide for easy temporary removal and replacement of the eye shield or eyelid splint when necessary.

It is yet a further object to provide a eye shield or eyelid splint retention system that will give the user the option of using the strap in the same manner as the known strap systems are used or with the enhanced retention security obtainable with the retention system embodying the present invention.

These and other objects of the invention will be apparent from the following disclosure of the preferred embodiments of the present invention.

SUMMARY OF THE INVENTION

The present invention comprises an improved eye shield retention system that holds a generally ovate eye cover in position across the bony orbital rim of a user's eye. The eye shield comprises a plastic shell adapted to function as an eye shield or as a backup member for an eyelid compress. The retention system has a first strap segment that attaches to the lower end of the eye shield and joins with a second strap segment behind the user's head. The second strap segment attaches to the upper end of the eye shield and is bifurcated into an upper and lower strap segment adapted to encircle a user's head either in an adjacent and parallel relationship or to be laterally separated to cause the two strap segments to oppose one another against the curvature of the user's skull. In the latter condition the strap segments prevent the eye shield retention system from slipping into a less than snug fit over the skull in which the eye cover could become dislodged. The invention further includes various modifications of this retention system such as both the first and second strap segments being bifurcated or such as the strap retention system comprising a continuous strap with one segment bifurcated and the other being a solid piece.

BRIEF DESCRIPTION OF THE DRAWINGS

The invention is best understood with reference to the drawings, in which:

FIG. 4 is a plan view of the embodiment of the eye shield retention system shown in FIG. 1;

FIG. 5 is a fragmentary view of a modification of the connection of the strap to the eye shield;

FIG. 6 is a vertical section view taken on the line 6—6 of FIG. 4;

FIG. 7 is a perspective view of an eye shield strap retention system embodying an alternative embodiment of the present invention;

FIG. 8 is a perspective view of an eye shield strap retention system embodying another alternative embodiment of the present invention.

DETAILED DESCRIPTION OF THE INVENTION

Figure 1:
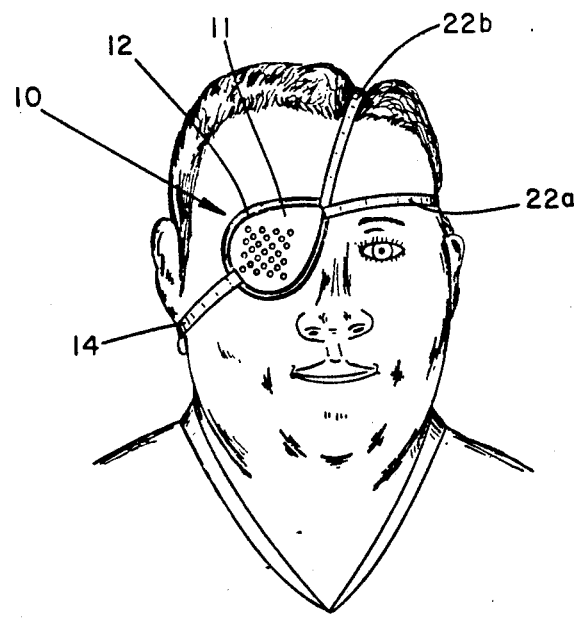
FIG. 1 is a front view showing one embodiment of the eye shield retention system of the present invention in place on the head of a user worn according to one method of use.

Referring first to FIG. 1, a strap retention system, generally designated 10, for holding an eye shield is shown covering one eye of user's head. The strap retention system 10 comprises an eye shield having a substantially ovate shell 11 provided with a peripheral elastomeric cushion 12 adapted to cushion the shell from the user's face. The shell 11 is preferably made from a plastic material or a light weight metal such as aluminum. The shell 11 has a slightly convex exterior surface and a slightly concave interior surface as shown in FIG. 6 and is of substantially uniform thickness providing a space between its interior surface and the eye of the user.

Figure 2:
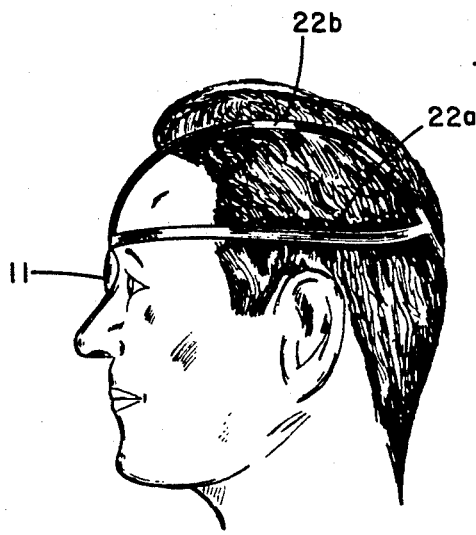
FIG. 2 is a side view of FIG. 1.
Figure 3:
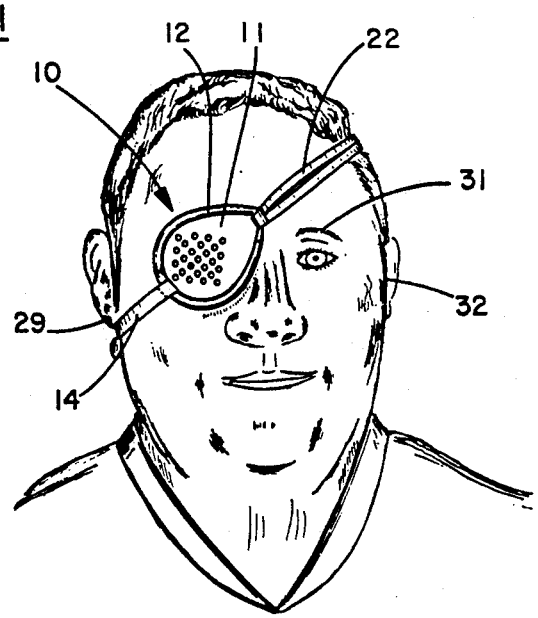
FIG. 3 is a front view in part similar to FIG. 1 showing one embodiment of the eye shield retention system of the present invention in place on the head of a user worn according to a second method of use.

The eye shield is generally worn in a diagonal or angled orientation with its upper end 19 positioned at the top of the inside of the user's eye near the nose and its lower end 17 positioned at the bottom of the outside of the user's eye, as shown in FIGS. 1-3.

The shell 11 preferably includes a plurality of ventilation holes 13. While these holes or apertures are generally covered up when the eye shield is used as an eyelid splint compress backup member, as described in Leonardi's U.S. Pat. Nos. 4,677,974 and No. 4,727,869, the holes may be used to look through when the device is used solely as an eye shield.

As shown in FIG. 4, the strap retention system 10 comprises a first strap member 14 that has an end portion 15 looped through a rectangular slot 16 at the lower end 17 of the shell 11. The overlapped portion of the end of the member 14 is secured back upon itself in any suitable manner such as stitching 18. Snap fasteners or Velcro type hooks and loops may be used in the place of the stitching.

At its upper end 19, the shell 11 has a rectangular slot 21 through which a second strap member 22 is attached to the shell 11. The second strap member 22 is bifurcated into a pair of generally identical individual segments—lower strap segment 22a and upper strap segment 22b. Each segment 22a and 22b is looped through the slot 21 with the overlapping portion of each segment secured back upon itself by stitching 23 or other suitable fasteners.

The opposite end portions 24 and 25 of the segments 22a and 22b are secured to a connecting element 26 in any suitable manner. The connecting element 26 is preferably is a rectangular piece of backing material with Velcro type fastener hoops and loops 27. For several inches of its length, the opposite end portion 28 of the first strap member 14 is also covered with Velcro type hooks and loops 27 for engagement with the hooks and loops on the connecting element 26. Mechanical fasteners such as snap fasteners could be used. The Velcro type fasteners, however, are well known in the industry and are preferred because of the ease of attachment and ease of adjustment.

Eye shields embodying the present invention are designed to fit either eye of a prospective user. In applying the eye shield to the head or skull, two options are presented. First, it may be decided that the first strap member 14 of FIG. 4 should be passed underneath the user's ear and around the back of the user's head. The second strap member 22 should be oriented so that the two strap segments 22a and 22b of the second strap member are placed adjacent to one another with no lateral separation. The user may decide that this orientation provides sufficient security to hold the eye shield in place and provides the best cosmetic appearance.

This orientation is shown in FIG. 3 and is achieved as follows: The first and second strap members are brought around for fastening across the back part of the head or skull. The first strap member 14 is passed below the user's temple either across or below the ear lobe 29. The second strap member 22 is passed above the non-protected eye 31, across the forehead and above the opposite ear 32. The strap segments 22a and 22b remain side-by-side as shown.

During sleep, however, the second strap member 22 tends to slide downward toward the opposite ear 32 due to friction of the user's head against a pillow. Because head circumference is generally smaller at the ear level, the strap retention system 10 becomes loose and the eye shield 11 has a tendency to slip off the eye. To provide a more positive retention system, the lower strap segment 22a may be separated by 2 or more inches from the upper strap segment 22b about the curvature of the head as shown in FIGS. 1 and 2. This is done by sliding lower strap segment 22a down toward the opposite ear 32 and by sliding upper strap segment 22b up toward the apex of the head.

With this orientation, strap segments 22a and 22b will then oppose one another against the curvature of the skull and become extremely effective at preventing the strap retention system 10 from slipping even during vigorous motion on a pillow. A snug fit is therefore comfortably maintained and the eye shield remains securely in place over the vulnerable eye.

Since the shell 11 of the eye shield is quite similar to the backing member for the compress eye splint disclosed in Leonardi's above-cited patents, the strap retention system of the present invention would be applicable for use with the earlier patented eye splints.

FIG. 5 shows a modification of the attachment of the strap segments 22a and 22b to the shell 11. Instead of each of the individual ends of the strips being looped through the slot 21 in the shell 11, a short strap attachment piece 31 is looped through the slot 21 and stitched or otherwise fastened in place. Snap fasteners or Velcro type hooks and loops may be used in the place of the stitching. The short strap attachment piece 31 is longitudinally split to provide two attachment legs 33 to which end portions of the strap segments 22a and 22b are stitched.

FIG. 7 shows an alternate embodiment of the strap retention system of the present invention. This alternate strap retention system 100 comprises an eye shield having a substantially ovate shell 111 provided with a peripheral elastomeric cushion 112 adapted to cushion the shell from the user's face. The shell 111 preferably includes a plurality of ventilation holes 113. The eye shield is generally worn in a diagonal or angled orientation with its upper end 119 positioned at the top of the inside of the user's eye near the nose and its lower end 117 positioned at the bottom of the outside of the user's eye.

As shown in FIG. 7, the strap retention system 100 further comprises a first strap member 114 that has a first end portion 115 looped through a rectangular slot at the lower end 117 of the shell 111. The overlapping first end portion 115 of the first strap member 114 is secured back upon itself in any suitable manner such as Velcro type hooks and loops.

At its upper end 119, the shell 111 has a rectangular slot through which a second strap member 122 is attached to the shell 111. The second strap member 122 is bifurcated into a pair of generally identical individual segments—lower strap segment 122a and upper strap segment 122b. A first end portion 131 of the second strap member 122 is likewise looped through a rectangular slot with the overlapping first end portion 131 secured back upon itself by any suitable manner such as Velcro type hooks and loops.

The opposite end 124 of the first strap member 114 and the opposite end 125 of the second strap member 122 are secured together at a location which would be on the backside of the user's head in any suitable manner such as stitching 129 as shown in FIG. 7. The bifurcated strap segments 122a and 122b join together just prior to the position at which the opposite end of the second strap member 222 is joined to the opposite end of the first strap member 114.

In the embodiment shown in FIG. 7, the first strap member 114 extends from the lower end 117 of the eye shield and can be looped around and under the user's ear. The second strap member 122 extends from the upper end 119 of the eye shield and lower strap segment 122a can be separated from upper strap segment 122b (as shown in FIG. 1) to securely hold the strap retention system on the head of the user. Any necessary or desired adjustment in the overall length and tightness of the strap retention system can be effected through the positioning of the overlapping end portions 115 and 131.

Another embodiment of the present invention is shown in FIG. 8. This alternate strap retention system 200 includes an eye shield having a substantially ovate shell 211 provided with a peripheral elastomeric cushion 212 adapted to cushion the shell from the user's face. The shell 211 preferably includes a plurality of ventilation holes 213. The eye shield is generally worn in a diagonal or angled orientation with its upper end 219 positioned at the top of the inside of the user's eye near the nose and its lower end 217 positioned at the bottom of the outside of the user's eye.

The strap retention system 200 further comprises a first strap member 214 that is bifurcated into a pair of generally identical individual strap segments—lower strap segment 214a and upper strap segment 214b. The first strap member also has a first end portion 215 looped through a rectangular slot at the lower end 217 of the shell 211. The overlapping first end portion 215 of the first strap member. 214 is secured back upon itself in any suitable manner such as Velcro type hooks and loops.

At its upper end 219, the shell 211 has a rectangular slot through which a second strap member 222 is attached to the shell 111. The second strap member 222 is bifurcated into a pair of generally identical individual strap segments—lower strap segment 222a and upper strap segment 222b. A first end portion 231 of the second strap member 222 is likewise looped through a rectangular slot with the overlapping first end portion 231 secured back upon itself by any suitable manner such as Velcro type hooks and loops.

The opposite end 224 of the first strap member 214 and the opposite end 225 of the second strap member 222 are secured together at a location which would be on the backside of the user's head in any suitable manner such as stitching 229 as shown in FIG. 8. The bifurcated strap segments 214a and 214b join together just prior to the position at which the opposite end of the first strap member 214 is joined to the opposite end of the second strap member 222. Similarly, the bifurcated strap segments 222a and 222b join together just prior to the position at which the opposite end of the second strap member 222 is joined to the opposite end of the first strap member 214.

In the embodiment shown in FIG. 8, the first strap member 214 extends from the lower end 217 of the eye shield and can be looped around and under the user's ear. The lower strap segment 222a can be separated from the upper strap segment 222b (similar to what is shown in FIG. 1) to securely hold the strap retention system on the head of the user. The second strap member 222 extends from the upper end 219 of the eye shield and the lower strap segment 222a can be separated from the upper strap segment 222b (also as shown in FIG. 1) to securely hold the strap retention system on the head of the user. This version effectively provides four straps segments for additionally holding force of the strap retention system. Any necessary or desired adjustment in the overall length and tightness of the strap retention system can be effected through the positioning of the overlapping end portions 215 and 231.

Figure 9:
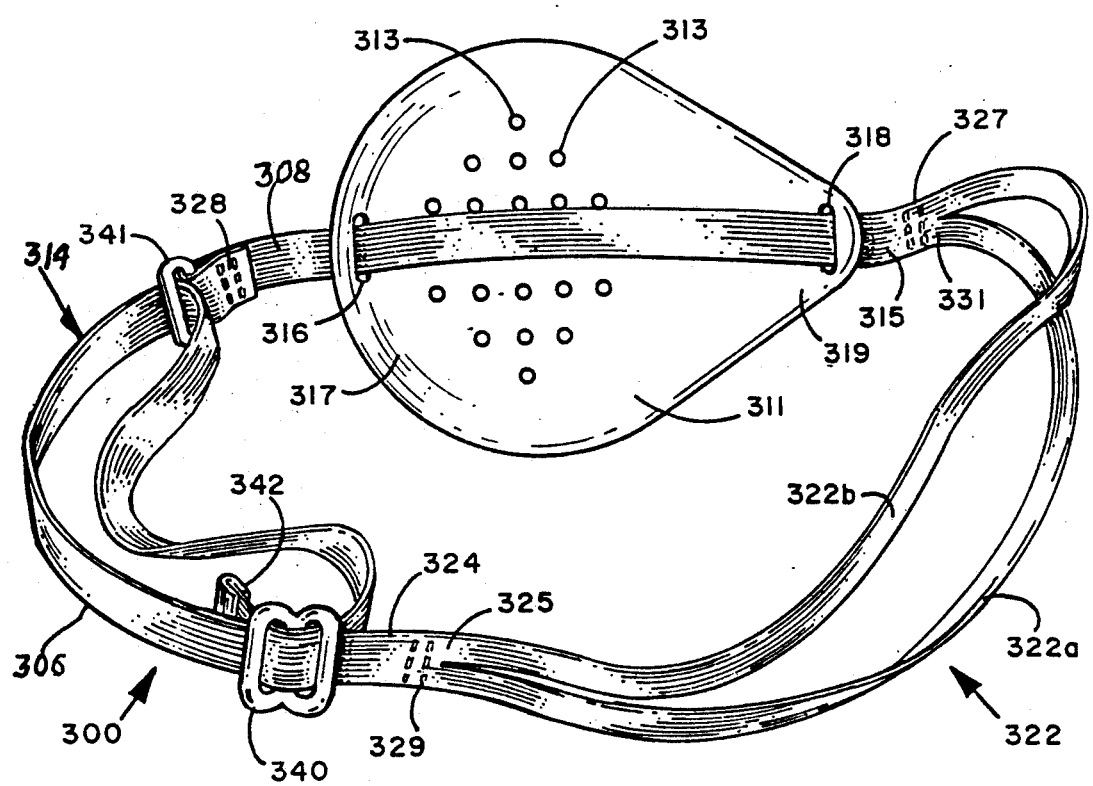
FIG. 9 is a perspective view of an eye shield strap retention system embodying another alternative embodiment of the present invention.

Yet another embodiment of the present invention is shown in FIG. 9. This alternate strap retention system 300 includes an eye shield having a substantially ovate shell 311 but the peripheral elastomeric cushion has been deleted from this drawing, although it can be included if desired. The shell 311 preferably includes a plurality of ventilation holes 313. The eye shield is generally worn in a diagonal or angled orientation with its upper end 319 positioned at the top of the inside of the user's eye near the nose and its lower end 317 positioned at the bottom of the outside of the user's eye.

The strap retention system 300 further comprises a first strap member 314 that is a non-bifurcated piece and comprises two sections—a looped section 306 and a straight section 308. The straight section 308 is joined to and extends through the eye shield by means of a lower slot 316 and an upper slot 318. The second end of the straight section 306 passes through a ring loop 341 and is stitched or otherwise attached back to itself at 328. The looped section 306 of the first strap member 314 passes through the ring loop 341 and is attached to the D-ring 340 in a conventional manner. This arrangement allows the first strap member 314 to be adjustable in length by the movement of the D-ring 340. The stop clip 342 prevents the looped section 306 from separating from the D-ring 340.

The strap retention system further includes a second strap member 322 which is bifurcated into a pair of generally identical individual strap segments—lower strap segment 322a and upper strap segment 322b.

A first end portion 331 of the second strap member 322 is attached to the first end portion 315 of the first strap member by means of any suitable fastener such as stitching 327. In the preferred embodiment of the invention, the joining of the first end portion 331 of the second strap member 322 to the first end portion 315 of the first strap member should effect an integral or continuous piece so that the ability of the strap retention system to slide through the slots 316 and 318 is not hampered. This joining preferably occurs adjacent the upper end 319 of the eye shield.

The opposite end 324 of the first strap member 314 and the opposite end 325 of the second strap member 322 are secured together at a location which would be on the backside of the user's head in any suitable manner such as stitching 329 as shown in FIG. 9. Alternatively, instead of the stitching 329 shown, these two ends can be joined by Velcro type hooks and loops as shown in FIG. 4 if an adjustable connection is desired. The bifurcated strap segments 322a and 322b join together just prior to the position at which the opposite end of the second strap member 322 is joined to the opposite end of the first strap member 314.

In the embodiment shown in FIG. 9, the first strap member 314 extends from the lower end 317 of the eye shield and can be looped around and under the user's ear. The second strap member 322 extends from the upper end 319 of the eye shield and the lower strap segment 322a can be separated from the upper strap segment 322b (also as shown in FIG. 1) to securely hold the strap retention system on the head of the user. Any necessary adjustment in the overall length and tightness of the strap retention system can be effected through the positioning of the sliding D-ring 340 which effects a lengthening or shortening of the first strap member 314.

The various strap elements of the present invention can be made from any suitable material, but preferably elastic strap material is used to allow a certain amount of stretching or contraction of the strap elements for users who have heads of varying sizes. Thus, the first strap and the second strap flexibly fit over the curvature of the user's skull in spaced relation to one another whereby the second strap coacts with the first strap to prevent the strap retention system from slipping into a loosened retention of the eye shield.

While the invention has been illustrated with respect to a specific embodiment thereof, this embodiment should be considered as illustrative rather than limiting. Various modifications and additions may be made and will be apparent to those skilled in the art. Accordingly, the invention should not be limited by the foregoing description, but rather should be defined only by the following claims.

What is claimed is:

1. A strap retention system for holding an eye shield on a user's head across the bony orbital rim of the user's eye, the eye shield positioned to have an upper end extending above the eye to be protected and a lower end extending below the eye to be protected, comprising:
   a) a first strap having a first end and a second end,
   b) a second strap having a first end and a second end,
   c) means for attaching the first end of the first strap to a lower portion of the eye shield,
   d) means for attaching the first end of the second strap to an upper portion of the eye shield,
   e) means for connecting the second end of the first strap to the second end of the second strap at a location at the approximate rear of the user's head, and
   f) the second strap being bifurcated intermediate its first end and second end into an upper strap segment and a lower strap segment so that the second strap member can encircle the user's head from the upper portion of the eye shield to the connection location at the approximate rear of the user's head, whereby the separation of the upper strap segment from the lower strap segment on the second strap member prevents the upper strap segment and the lower strap segment from slipping from the user's head such that the strap retention system would become loosened enough to allow the eye shield to become dislodged from the user's eye.

2. The strap retention system of claim 1 wherein the upper strap segment and the lower strap segment are laterally separable for at least two inches.

3. The strap retention system of claim 1 wherein the first strap and the second strap are each elastic and flexibly fit over the curvature of the user's skull in spaced relation to one another whereby the second strap coacts with the first strap to prevent the strap retention system from slipping into a loosened retention of the eye shield.

4. The strap retention system of claim 1 wherein the means for attaching the first end of the first strap to the lower portion of the eye shield comprises the first end looped through a slot on the eye shield and stitched back upon itself and the means for attaching the first end of the second strap to the upper portion of the eye shield comprises the first end looped through a slot on the eye shield and stitched back upon itself.

5. The strap retention system of claim 4 wherein the means for connecting the second end of the first strap to the second end of the second strap at a location at the approximate rear of the user's head is hooks and loops.

6. The strap retention system of claim 1 wherein the means for attaching the first end of the first strap to the lower portion of the eye shield comprises the first end looped through a slot on the eye shield and connected by hooks and loops back upon itself and the means for attaching the first end of the second strap to the upper portion of the eye shield comprises the first end looped through a slot on the eye shield and connected by hooks and loops back upon itself.

7. The strap retention system of claim 6 wherein the means for connecting the second end of the first strap to the second end of the second strap at a location at the approximate rear of the user's head is stitching.

8. A strap retention system for holding an eye shield on a user's head across the bony orbital rim of the user's eye, the eye shield positioned to have an upper end extending above the eye to be protected and a lower end extending below the eye to be protected, comprising:
   a) a first strap having a first end and a second end,
   b) a second strap having a first end and a second end, the second strap being bifurcated from its first end to its second end along its entire length into an upper strap segment and a lower strap segment,
   c) means for attaching the first end of the first strap to a lower portion of the eye shield,
   d) means for attaching a first end of the upper strap segment of the second strap to an upper portion of the eye shield,
   e) means for attaching a first end of the lower strap segment of the second strap to an upper portion of the eye shield adjacent to the first end of the upper strap segment but independently therefrom so that each of the lower strap segment and the upper strap segment can move independently to provide more secure retention,
   f) means for connecting the second end of the first strap to the second end of the second strap at a location at the approximate rear of the user's head so that the second strap member can encircle the user's head from the upper portion of the eye shield to the connection location at the approximate rear of the user's head, whereby the separation of the upper strap segment from the lower strap segment on the second strap member prevents the upper strap segment and the lower strap segment from slipping from the user's head such that the strap retention system would become loosened enough to allow the eye shield to become dislodged from the user's eye.

9. The strap retention system of claim 8 wherein the upper strap segment and the lower strap segment are capable of being laterally separated for at least two inches.

10. The strap retention system of claim 8 wherein the first strap and the second strap are each elastic and flexibly fit over the curvature of the user's skull in spaced relation to one another whereby the second strap coacts with the first strap to prevent the strap retention system from slipping into a loosened retention of the eye shield.

11. A strap retention system for holding an eye shield on a user's head across the bony orbital rim of the user's eye, the eye shield positioned to have an upper end extending above the eye to be protected and a lower end extending below the eye to be protected, comprising:
   a) a first strap having a first end and a second end,
   b) a second strap having a first end and a second end,
   c) means for attaching the first end of the first strap to a lower portion of the eye shield,
   d) means for attaching the first end of the second strap to an upper portion of the eye shield,
   e) means for connecting the second end of the first strap to the second end of the second strap at a location at the approximate rear of the user's head, f) the first strap being bifurcated intermediate its first end and second end into an upper strap segment and a lower strap segment so that the first strap member can encircle the user's head from the lower portion of the eye shield to the connection location at the approximate rear of the user's head, and f) the second strap being bifurcated intermediate its first end and second end into an upper strap segment and a lower strap segment so that the second strap member can encircle the user's head from the upper portion of the eye shield to the connection location at the approximate rear of the user's head, whereby the separation of the upper strap segment from the lower strap segment on the first strap member and the separation of the upper strap segment from the lower strap segment on the second strap member combine to prevent the upper strap segments and the lower strap segments from slipping from the user's head such that the strap retention system would become loosened enough to allow the eye shield to become dislodged from the user's eye.

12. The strap retention system of claim 11 wherein each upper strap segment and the lower strap segment are laterally separable from each other for at least two inches.

13. The strap retention system of claim 11 wherein the first strap and the second strap are each elastic and flexibly fit over the curvature of the user's skull in spaced relation to one another whereby the second strap coacts with the first strap to prevent the strap retention system from slipping into a loosened retention of the eye shield.

14. The strap retention system of claim 11 wherein the means for attaching the first end of the first strap to the lower portion of the eye shield comprises the first end looped through a slot on the eye shield and connected by hooks and loops back upon itself and the means for attaching the first end of the second strap to the upper portion of the eye shield comprises the first end looped through a slot on the eye shield and connected by hooks and loops back upon itself.

15. The strap retention system of claim 14 wherein the means for connecting the second end of the first strap to the second end of the second strap at a location at the approximate rear of the user's head is stitching.

16. A strap retention system for holding an eye shield on a user's head across the bony orbital rim of the user's eye, the eye shield positioned to have an upper end extending above the eye to be protected and a lower end extending below the eye to be protected, comprising:
a) a first strap having a first end and a second end,
b) a second strap having a first end and a second end,
c) a lower slot on the lower portion of the eye shield and an upper slot on the upper portion of the eye shield, the first strap being disposed thorough the lower slot and the upper slot,
d) the first end of the first strap attached to the first end of the second strap at a location adjacent the upper slot,
e) the second end of the first strap attached to the second end of the second strap at a location at the approximate rear of the user's head,
f) the second strap being bifurcated intermediate its first end and second end into an upper strap segment and a lower strap segment so that the second strap member can encircle the user's head from the upper portion of the eye shield to the connection location at the approximate rear of the user's head, whereby the separation of the upper strap segment from the lower strap segment on the second strap member combine to prevent the upper strap segment and the lower strap segment from slipping from the user's head such that the strap retention system would become loosened enough to allow the eye shield to become dislodged from the user's eye.

17. The strap retention system of claim 16 wherein the upper strap segment and the lower strap segment are capable of being laterally separated from each other for at least two inches.

18. The strap retention system of claim 16 wherein the first strap and the second strap are each elastic and flexibly fit over the curvature of the user's skull in spaced relation to one another whereby the second strap coacts with the first strap to prevent the strap retention system from slipping into a loosened retention of the eye shield.

19. The strap retention system of claim 16 wherein the first end of the first strap is attached to the first end of the second strap by stitching so that the attachment effects a continuous piece so that the ability of the strap retention system can slide through the upper and lower slots.

20. The strap retention system of claim 16 wherein the second end of the first strap is attached to the second end of the second strap by stitching.

21. The strap retention system of claim 16 wherein the second end of the first strap is attached to the second end of the second strap by hooks and loops.

22. The strap retention system of claim 16 including means for adjusting the length of the first strap member.

23. The strap retention system of claim 16 wherein the means for adjusting the length of the first strap member is a D-ring.

24. An eye shield retention system for holding an eye shield in place across the orbital rim of a user's eye comprising:
a) an eye shield having an upper end and a lower end, and
b) a strap attached to the eye shield, the strap comprising:
1) a first strap segment attached at its first end to the lower end of the eye shield,
2) a second strap segment attached at its first end to the upper end of the eye shield, the second strap segment being bifurcated along its entire length into an upper strap segment and a lower strap segment, and
3) means for attaching a first end of the upper s trap segment of the second strap segment to an upper portion of the eye shield adjacent to the first end of the upper strap segment but independently therefrom so that each of the lower strap segment and the upper strap segment can move independently to provide more secure retention, and
5) means for joining a second end of the first strap segment to a second end of the second strap segment whereby when the eye shield retention system is disposed around the head of a user, the first strap segment extends from the lower end of the eye shield around one side of the user's head and the second strap segment extends from the upper end of the eye shield around the other side of the user's head, the second strap being bifurcated so that the upper strap segment extends over the top of the user's head and the lower strap segment extends around the side of the user's head such that the eye shield is retained on the user's head by at least a three-directional support.

25. An eye shield retention system for holding an eye shield in place across the orbital rim of a user's eye comprising:
   a) an eye shield having an upper end and a lower end, and
   b) a strap attached to the eye shield, the strap comprising:
      1) a first strap segment attached at its first end to the lower end of the eye shield,
      2) a second strap segment attached at its first end to the upper end of the eye shield, the second strap segment being bifurcated intermediate its first end and second end into an upper strap segment and a lower strap segment, and
      3) means for joining a second end of the first strap segment to a second end of the second strap segment whereby when the eye shield retention system is disposed around the head of a user, the first strap segment extends from the lower end of the eye shield around one side of the user's head and the second strap segment extends from the upper end of the eye shield around the other side of the user's head, the second strap being bifurcated so that the upper strap segment extends over the top of the user's head and the lower strap segment extends around the side of the user's head such that the eye shield is retained on the user's head by at least a three-directional support.

* * * * *